United States Patent [19]

Bantick et al.

[11] Patent Number: 4,518,612
[45] Date of Patent: May 21, 1985

[54] NAPHTHALENE AND 2-OXO-BENZOPYRAN ACIDS AND DERIVATIVES AND PHARAMACEUTICAL USE THEREOF

[75] Inventors: John R. Bantick, Loughborough; John Fuher, Alvaston; David N. Hardern; Thomas B. Lee, both of Loughborough, all of England

[73] Assignee: Fisons plc, Ipswich, England

[21] Appl. No.: 563,709

[22] Filed: Dec. 21, 1983

Related U.S. Application Data

[62] Division of Ser. No. 359,817, Mar. 19, 1982, Pat. No. 4,424,231.

[30] Foreign Application Priority Data

Mar. 24, 1981 [GB] United Kingdom ............... 8109090
Jul. 1, 1981 [GB] United Kingdom ............... 8120255

[51] Int. Cl.³ ............... A61K 31/19; A61K 31/35; C07C 65/11; C07D 311/12
[52] U.S. Cl. ............... 514/457; 514/533; 514/535; 514/538; 514/543; 514/567; 549/283; 549/285; 549/287; 549/289; 560/10; 560/45; 560/51; 560/53; 560/54; 560/56; 562/427; 562/433; 562/452; 562/461; 562/466; 562/467; 514/569
[58] Field of Search ............... 549/283, 285, 281, 289; 560/10, 45, 51, 53, 54, 56; 562/427, 433, 452, 461, 466, 467; 564/162, 163, 167, 169, 172; 424/279, 308, 309, 317, 319, 324

[56] References Cited

U.S. PATENT DOCUMENTS 3,882,148 5/1975 Augstein et al. ............... 424/283 X

FOREIGN PATENT DOCUMENTS 1144906 3/1969 United Kingdom .

Primary Examiner—Richard L. Raymond
Attorney, Agent, or Firm—Marshall, O'Toole, Gerstein, Murray & Bicknell

[57] ABSTRACT

There are described compounds of formula I,

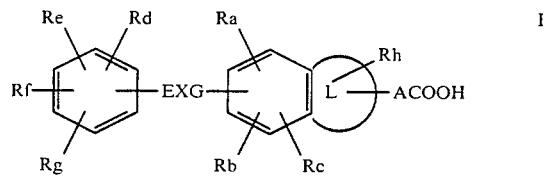

in which
$R_a$, $R_b$, $R_c$, $R_d$, $R_e$, $R_f$ and $R_g$, which may be the same or different, each represent hydrogen, amino, hydroxy, alkoxy, alkenyloxy, halogen, acyl, alkenyl, alkyl, or alkoxy substituted by phenyl,
$R_h$ is hydrogen, alkyl or —COOH.
X is a hydrocarbon chain containing from 2 to 10 carbon atoms and optionally substituted by a hydroxy group,
A has no significance or represents Y, OY, or SY and Y represents a C 1 to 4 hydrocarbon chain which is optionally substituted by alkyl C 1 to 4,
E and G, which may be the same or different, each represent —O—, —S— or —CH₂—, provided that at least one of E and G is —O— or —S—,
L, together with the carbon atoms to which it is attached, forms a benzene, furan, thiophene, pyrrole, or pyran-2-one ring,
and pharmaceutically acceptable derivatives thereof.

11 Claims, No Drawings

NAPHTHALENE AND 2-OXO-BENZOPYRAN ACIDS AND DERIVATIVES AND PHARAMACEUTICAL USE THEREOF

This is a division of application Ser. No. 359,817, filed Mar. 19, 1982, U.S. Pat. No. 4,424,231.

This invention relates to new compounds, methods for their preparation and compositions containing them.

According to our invention we provide compounds of formula I,

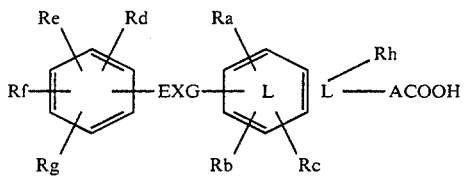

in which

Ra, Rb, Rc, Rd, Re, Rf and Rg, which may be the same or different, each represent hydrogen, amino, hydroxy, alkoxy, alkenyloxy, halogen, acyl, alkenyl, alkyl, or alkoxy substituted by phenyl, Rh is hydrogen, alkyl or —COOH, X is a hydrocarbon chain containing from 2 to 10 carbon atoms and optionally substituted by a hydroxy group, A has no significance or represents Y, OY, or SY and Y represents a C 1 to 4 hydrocarbon chain which is optionally substituted by alkyl C 1 to 4, E and G, which may be the same or different, each represent —O—, —S— or —CH$_2$—, provided that at least one of E and G is —O— or —S—, L, together with the carbon atoms to which it is attached, forms a benzene, furan, thiophene, pyrrole or pyran-2-one ring, and pharmaceutically acceptable derivatives thereof.

According to the invention we also provide the compounds of the formula I, and pharmaceutically acceptable derivatives thereof, for use as pharmaceuticals.

According to our invention we further provide a process for the production of a compound of formula I, or a pharmaceutically acceptable derivative thereof, which comprises (a) reacting a compound of formula II,

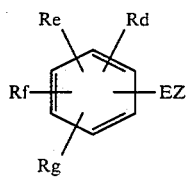

in which

E, Rd, Re, Rf and Rg are as defined above, and Z is hydrogen or a reactive metal when E is —O— or —S—, or a hydrocarbon chain containing from 2 to 10 carbon atoms and carrying an anion forming group, an epoxide group or an activated alcohol group, with a compound for formula III,

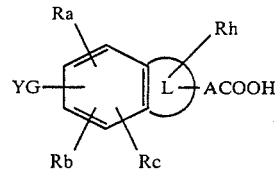

or an ester thereof, in which

A,G, Ra, Rb, Rc, L and Rh are as defined above, and Y represents hydrogen or a reactive metal when G is —O— or —S— and when Z represents a hydrocarbon chain containing from 2 to 10 carbon atoms carrying an anion forming group, an epoxide group or an activated alcohol group, and when Z represents hydrogen or a reactive metal and E is —O— or —S—, Y represents a hydrocarbon chain containing from 2 to 10 carbon atoms and carrying an anion forming group, an epoxide group or an activated alcohol group, (b) producing a compound of formula I in free acid form by hydrolysing a compound of formula IV,

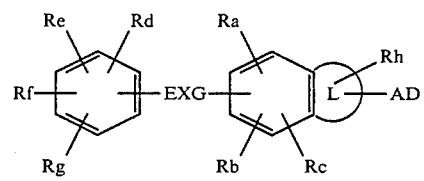

in which

A, E, X, G, L, Ra, Rb, Rc, Rd, Re, Rf, Rg and Rh are as defined above, and

D represents a group hydrolyseable to a —COOH group (c) producing a compound of formula I, or an ester thereof, in which at least one of Ra to Rg is alkoxy or alkenyloxy, by selective alkoxylation or alkenyloxylation of a corresponding compound of formula I, or an ester thereof, in which at least one of Ra to Rh is hydroxy, (d) producing a compound of formula I, or an ester thereof, in which a pair of Rd to Rg represent hydroxy and alkenyl, by subjecting a corresponding compound of formula I, or an ester thereof, in which a pair of Rd to Rg represent alkenyloxy and hydrogen, to an elevated temperature, or (e) producing a compound of formula Ia,

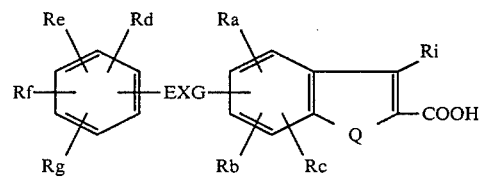

or an ester thereof, in which

Ra, Rb, Rc, Rd, Re, Rf, Rg, E, X and G are as defined above,

Ri is hydrogen or alkyl, and

Q is —S— or —O—, by cyclisation of a compound of formula V,

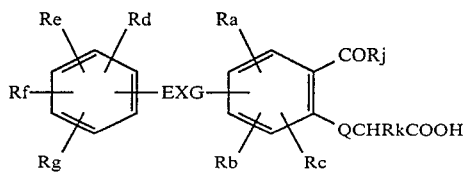

or an ester thereof, in which

Ra, Rb, Rc, Rd, Re, Rf, Rg, E, X, G and Q are as defined above,

Rj is hydrogen or alkyl, and

Rk is hydrogen or —COOH, and when Rk is —COOH, or an ester thereof, subsequent decarboxylation and dehydration, and where desired or necessary converting the compound of formula I to a pharmaceutically acceptable derivative thereof, or vice versa.

In process (a) when Y or Z is a reactive metal the metal may be, for example, an alkali metal, e.g. sodium or another reactive metal, e.g. thallium. We prefer Y or Z not to be a reactive metal when E or G is respectively a group —CH$_2$—. When Y or Z represent a hydrocarbon chain carrying an anion forming group the anion forming group may be, for example, a halogen atom, e.g. bromine, or a sulphonate group, e.g. a methyl sulphonate or a p-toluenesulphonate group. When Y or Z represents a hydrocarbon chain carrying a halogen atom the reaction may be carried out in the presence of a solvent which is inert under the reaction conditions, e.g. acetone, dimethylformamide or tetrahydrofuran and in the presence of an acid acceptor, e.g. potassium carbonate or sodium hydride. The reaction is also preferably carried out under anhydrous conditions and in the presence of a suitable catalyst, e.g. KI. When Y or Z represent a hydrocarbon group carrying an epoxide the reaction may be carried out at an elevated temperature in a solvent which is inert under the reaction conditions, e.g. dioxan or dimethylformamide, and in the presence of a suitable catalyst, e.g. trimethylbenzylammonium hydroxide. Alternatively the reaction may be carried out at an elevated temperature in a tertiary alcohol, e.g. t-butanol or 1,1-dimethylpropan-1-ol and in the presence of the potassium salt of the alcohol. As a further alternative the reaction may be carried out in the presence of an alkali metal hydroxide in an alkanol, e.g. ethanol.

In process (b) the group D may be, for example, an ester, amide or nitrile group, which may be hydrolysed to a —COOH group. The hydrolysis may be carried out using conventional techniques, for example, under acidic or mildly basic conditions, e.g. using sodium bicarbonate.

In process (c) the alkylating or alkenylating agent may be an alkyl or alkenyl group connected to a good amionic leaving group, e.g. a halide (bromide) or toluene sulphonate group. The reaction may be carried out in a solvent which is inert under the reaction conditions, e.g. dimethylformamide or acetone and in the presence of an acid acceptor, e.g. sodium hydride or potassium carbonate.

Process (d) may be carried out at a temperature of from about 150° to 250°, and is preferably carried out under an inert atmosphere. The reaction may be carried out in the absence of a solvent or in the presence of a high boiling solvent, e.g. N-methylpyrrolidinone or diethylaniline.

The cyclisation of process (e) may be carried out in a solvent which is inert under the reaction conditions, e.g. dimethylformamide or acetone, and in the presence of a base, e.g. potassium carbonate or sodium hydride. The reaction may be carried out at a temperature of from about 20° to 100° C. When Rk is —COOH, or an ester thereof, the decarboxylation and dehydration may be carried out in the presence of HBr and acetic acid, e.g. at the reflux temperature of the reaction mixture.

Compounds of formulae II, III, IV and V are either known, or they may be made from known compounds using conventional techniques known per se or by processes similar to those described in the Examples. Thus, for example, compounds of formula IV may be made by a process analogous to process (a) above.

The processes as described above may produce the compound of formula I or a derivative thereof. It is also within the scope of this invention to treat any derivative so produced to liberate the free compound of formula I, or to convert one derivative into another.

The compounds of formula I and the intermediates therefor may be isolated from their reaction mixtures using conventional techniques.

Pharmaceutically acceptable derivatives of the compounds of formula I include pharmaceutically acceptable salts, esters and amides of any —COOH groups present. Suitable salts include ammonium, alkali metal (e.g. sodium, potassium and lithium) and alkaline earth metal (e.g. calcium or magnesium) salts, and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, with simple monocylcic nitrogen heterocyclic compounds, e.g. piperidine or morpholine, with an amino acid, e.g. lysine, ornithine, arginine, or an N-alkyl, especially an N-methyl derivative of any one thereof, or with an aminosugar, e.g. glucamine, N-methylglucamine or glucosamine. Suitable esters include simple lower alkyl esters, e.g. the ethyl ester, esters derived from alcohols containing basic groups, e.g. di-lower alkyl amino substituted alkanols such as the 2-(diethylamino)-ethyl ester, and acyloxy alkyl esters, e.g. a lower acyloxy-lower alkyl ester such as the pivaloyloxymethyl ester. The pharmaceutically acceptable acid addition salts of the basic esters, e.g. the hydrochloride, the hydrobromide, the maleate or the fumarate salts, may also be used. The esters may be made by conventional techniques, e.g. esterification or transesterification. The amides may be, for example, unsubstituted or mono- or di- C 1 to 6 alkyl or phenyl amides and may be made by conventional techniques, e.g. reaction of an ester of the corresponding acid with ammonia or an appropriate amine. Other pharmaceutically acceptable derivatives are compounds which will be suitable bioprecursors (prodrugs) of the compounds of formula I and will be readily apparent to those skilled in the art and may be made from the compounds of formula I using conventional processes know per se or by processes analogous to those described above. The compounds of formula I may, under certain circumstances, be metabolised within the body to form new compounds. These new metabolites are included within the ambit of the invention.

The compounds of formula I and their pharmaceutically acceptable derivatives possess pharmacological properties. In particular, they are antagonists of the slow reacting substance of anaphylaxis (SRS-A) or its pathological effects, as indicated by their activity in the test described by Augstein et al, Nature New Biology, 1973, 245, 215.

The compounds are thus indicated for use in the treatment of disorders in which SRS-A is a factor, for example skin afflictions, hay fever and obstructive airways diseases, e.g. asthma, coughs, bronchitis and bronchorrhea.

For the above mentioned uses, the dosage administered will, of course, vary depending upon the compound employed, mode of administration and treatment desired. However, in general satisfactory results are obtained when the compounds are administered at a daily dosage of from about 0.05 milligrams to about 10 milligrams per kilogram of animal body weight, preferably given in divided doses 2 to 4 times a day or in sustained release form. For the larger mammals, the total daily dosage is in the range of from about 1 milligram to about 700 milligrams and dosage forms suitable for administration comprise from about 12 milligrams to about 350 milligrams of the compound admixed with a solid or liquid pharmaceutical carrier or diluent. The compounds may be administered during or before the attack of the disorder to be treated.

The compounds of formula I and the pharmaceutically acceptable derivatives thereof, are more active, more stable, more selective, less toxic or possess less side effects when tested in certain pharmacological models, are more potent, have a different (e.g. longer) duration of action, have a different absorption profile (e.g. are better absorbed), are more easily formulated or possess other advantageous properties when compared to similar known compounds.

According to our invention we also provide a pharmaceutical composition comprising (preferably a minor proportion of) a compound of formula I, or a pharmaceutically acceptable derivatives thereof, in admixture with a pharmaceutically acceptable adjuvant, diluent or carrier. Examples of suitable adjuvants, diluents or carriers are: for tablets and dragées; lactose, starch, talc or stearic acid; for capsules, tartaric acid or lactose; for suppositories, natural or hardened oils or waxes; for inhalation a coarse carrier, e.g. lactose or a compressed gas propellant, e.g. a chlorofluorohydrocarbon, and optionally a surfactant; and for topical application, wool fat, soft paraffin or a cream BP. For use in such compositions, the compound of formula I, or the pharmaceutically acceptable derivative thereof, preferably has a mass median diameter of from 0.01 to 10 microns. The compositions may also contain suitable preserving, stabilising and wetting agents, solubilizers, sweetening and colouring agents and flavourings. The compositions may, if desired, be formulated in sustained release form. We prefer compositions which are designed to be administered by inhalation.

The groups Ra to Rh, when they contain carbon, preferably each contain less than 7, and more preferably 1 to 4, carbon atoms.

Specific significances which Ra to Rg may have, independantly, are hydrogen, acetyl, formyl, hydroxy, methyl, propyl, allyl, allyloxy and chlorine. We prefer none, or only one, of Ra, Rb and Rc to be other than hydrogen. We prefer two, three or four (and preferably three) of Rd, Re, Rf and Rg to be other than hydrogen. More specifically we prefer an adjacent three of Rd, Re, Rf and Rg to have different specific significances as given immediately above, e.g. to be acetyl, hydroxy and propyl.

We prefer Rh to be hydrogen or alkyl, e.g. methyl. When L forms an indole ring the nitrogen of the indole is unsubstituted.

We prefer A not to be present or to be Y or OY. We also prefer Y to be —CH$_2$— or —CH(CH$_3$)—.

Where one or more of Rd to Rg represent an alkyl group, it is preferably ortho to the —EXG— chain.

X preferably represents a straight chain saturated hydrocarbon group, containing 2 to 6, and preferably 3 carbon atoms; a particularly preferred group being trimethylene or 2-hydroxytrimethylene.

We prefer E and G both to be oxygen or one to be oxygen and the other sulphur.

A preferred group of compounds of formula I are those in which E and G are both oxygen, Ra, Rb and Rc each represent hydrogen, alkyl or alkenyl, Rd, Re, Rf and Rg, each represent hydrogen, hydroxy, alkoxy, acyl, alkenyl alkyl or alkoxy substituted by phenyl, Rh is hydrogen, A has no significance and L is a benzene ring.

A further preferred group of compounds are those in which E and G are both oxygen, Rg, Ra and Rb are all hydrogen, Rc, Rd, Re and Rf are hydrogen, hydroxy, alkanoyl, alkenyl or alkyl and the ring L, together with the group —A—COOH is of formula,

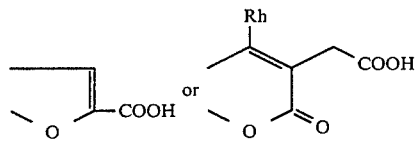

in which Rh is hydrogen or alkyl.

Certain of the compounds of formula I possess one or more chiral centres and the invention also provides the compounds in the form of their individual optical isomers or as racemic, or other, mixtures thereof. Certain of the compounds of formula I may also exist as cis or trans isomers and in these cases the invention provides both isomeric forms. The various isomers may be prepared and/or separated using conventional processes known per se.

The invention is illustrated but in no way limited by the following Examples in which temperatures are in °C.

EXAMPLE 1

Sodium 7-(3-[4-acetyl-3-hydroxy-2-proylphenoxy]-2-hydroxypropoxy)-8-propylnaphthalene-2-carboxylate (a) Ethyl 7-hydroxynaphthalene-2-carboxylate A solution of 7-hydroxynaphthalene-2-carboxylic acid (56.09 g) in ethanol (200 ml) was saturated with dry hydrogen chloride and then refluxed for 30 minutes. The mixture was evaporated to about half volume, treated with water, and extracted with ethyl acetate, which was washed with water, and sodium bicarbonate solution, dried and evaporated to give a solid. Crystallisation from ethyl acetate afforded ethyl 7-hydroxynaphthalene-2-carboxylate (37.5 g), m.p. 155°–156°.

Found: C, 72.1; H, 5.7. C$_{13}$H$_{12}$O$_3$ Requires: C, 72.2; H, 5.6%.

(b) Ethyl 7-allyloxynaphthalene-2-carboxylate

A mixture of ethyl 7-hydroxynaphthalene-2-carboxylate (37.5 g), anhydrous potassium carbonate (24.0 g), potassium iodide (0.5 g), and allyl bromide (29.0 g) was heated in refluxing acetone (200 ml) with stirring for 15 hours. The mixture was filtered and the filtrate was evaporated. The residue was dissolved in ethyl-acetate, washed with 2% sodium hydroxide solution and water, dried and evaporated to give a solid. Crystallisation from petroleum ether (b.p. 40–60) afforded ethyl 7-allyloxynaphthalene-2-carboxylate (36 g), m.p. 60°–61°.

Found: C, 74.7; H, 6.4. $C_{16}H_{16}O_3$ Requires: C, 75.0; H, 6.3%.

(c) Ethyl 8-allyl-7-hydroxynaphthalene-2-carboxylate

Ethyl 7-allyloxynaphthalene-2-carboxylate (6.2 g) was heated in refluxing N,N-diethylaniline for 2 hours. The solution was cooled, treated with dilute hydrochloric acid and extracted with ethyl acetate, which was then washed with dilute hydrochloric acid, and water, dried and evaporated to a solid. Crystallisation from benzene/petroleum ether (b.p. 40–60) afforded ethyl 8-allyl-7-hydroxynaphthalene-2-carboxylate (4.5 g); m.p. 115°–116°.

Found: C, 74.7; H, 6.3. $C_{16}H_{16}O_3$ Requires: C, 75.0; H, 6.3%.

(d) Ethyl 7-hydroxy-8-propylnaphthalene-2-carboxylate

Ethyl 8-allyl-7-hydroxynaphthalene-2-carboxylate (4 g) in ethanol was hydrogenated at 3 atmospheres in the presence of a 5% palladium charcoal catalyst for 1 hour. Filtration and evaporation of the filtrate gave a solid, which crystallised from benzene-petroleum ether (b.p. 60–80) to give ethyl 7-hydroxy-8-propylnaphthalene-2-carboxylate (3.2 g), m.p. 114°–115°.

Found: C, 74.2; H, 7.2. $C_{16}H_{18}O_3$ Requires: C, 74.4; H, 7.0%.

(e) 7-(3-[4-Acetyl-3-hydroxy-2-propylphenoxy)-2-hydroxypropoxy)-8-propylnaphthalene-2-carboxylic acid 4-(2,3-Epoxypropoxy)-2-hydroxy-3-propylacetophenone (27.6 g), ethyl 7-hydroxy-8-propylnaphthalene-2-carboxylate (25.8 g), and benzyltrimethylammonium hydroxide (10 drops) was heated under reflux in dimethylformamide (200 ml) for 50 hours at 100°. Evaporation of the solution gave an oil, which was dissolved in ethylacetate, washed with 2N sodium hydroxide solution, and water, dried and evaporated. The oily residue was chromatographed on silicic acid with dichloromethane. The main fraction was hydrolysed by heating with 20% aqueous sodium hydroxide in ethanol. Acidification gave an oil which crystallised from aqueous ethanol to furnish 7-(3-[4-acetyl-3-hydroxy-2-propylphenoxy]-2-hydroxypropoxy)-8-propylnaphthalene-2-carboxylic acid (11.6 g), m.p. 125°–126°.

Found: C, 69.1; H, 7.0. $C_{28}H_{32}O_7 \cdot \frac{1}{2}H_2O$ Requires: C, 68.7; H, 6.8%.

(f) Sodium 7-[3-(4-acetyl-3-hydroxy-2-propylphenoxy)-2-hydroxypropoxy]-8-propylnaphthalene-2-carboxylate 7-[3-(4-acetyl-3-hydroxy-2-propylphenoxy)-2-hydroxypropoxy]-8-propylnaphthalene-2-carboxylic acid (9.377 g) was treated with an aqueous solution of sodium bicarbonate (1.640 g) and the resulting solution was freeze-dried to afford sodium 7-[3-(4-acetyl-3-hydroxy-2-propylphenoxy)-2-hydroxypropoxy]-8-propylnaphthalene-2-carboxylate (8.4 g).

Found: C, 63.05; H, 6.4. $C_{28}H_{31}NaO_7 + 5.7\%$ $H_2O$ Requires: C, 63.05; H, 6.5%.

EXAMPLE 2

Sodium 6-[3-(4-acetyl-3-hydroxy-2-propylphenoxy)-2-hydroxypropoxy]-7-propylbenzofuran-2-carboxylate (a) 2,4-Dihydroxy-3-propylbenzaldehyde Zinc cyanide (24 g) was added to a stirred suspension of 2-propylresorcinol (32.4 g) in dry ether (150 ml) and the resulting mixture saturated with hydrogen chloride. After being left to stand at room temperature for 30 minutes the ether was decanted and the remaining solid heated on the steam bath with water for 30 minutes.

The aqueous solution was extracted with ethyl acetate and the organic phase evaporated to a black tar. Distillation gave 8.0 g of a yellow oil $bp_{0.2}$ 130°–140°.

(b) 4-Benzyloxy-3-propylsalicylaldehyde

A mixture of 2,4-dihydroxy-3-propylsalicylaldehyde (15.5 g), benzyl chloride (12.0 g), potassium carbonate (13 g) and potassium iodide (0.5 g) in dry acetone (350 ml) was heated under reflux for 24 hours. The solid was removed by filtration and the solution evaporated to dryness. The oil obtained was distilled and the fraction $bp_{0.5}$ mm 220–224° was collected to yield 15.0 g of 4-benzyloxy-3-propylsalicylaldehyde.

(c) Ethyl 2-(3-benzyloxy-6-formyl-2-propylphenoxy)acetate

A mixture of 4-benzyloxy-3-propylsalicylaldehyde (15.0 g) ethyl bromoacetate (10.2 g), potassium carbonate (8.4 g) and potassium iodide (0.5 g) in dry acetone (250 ml) was heated under reflux for 24 hours. The solid was removed by filtration and the solvent evaporated to leave ethyl 2-(3-benzyloxy-6-formyl-2-propylphenoxy) acetate (20.0 g) as a dark oil.

(d) Ethyl 6-benzyloxy-7-propylbenzofuran-2-carboxylate

Sodium ethoxide was prepared by dissolving metallic sodium (1.6 g) in dry ethanol (20 ml). The acetate product of step (c) (20 g) was added and the mixture heated under reflux for 15 minutes. The ethanol was removed and dilute hydrochloric acid added. The complete mixture obtained was hydrolysed with sodium carbonate by refluxing in ethanol/water for 1 hour. Water was added and the aqueous solution washed with ether. Acidification with dilute hydrochloric acid gave a purple solid. This acid was esterified by refluxing for 3 hours in ethanol saturated with hydrogen chloride. The solution was evaporated to dryness and ethyl acetate added. The solution was washed with sodium bicarbonate, dried over magnesium sulphate, filtered and evaporated to furnish ethyl 6-benzyloxy-7-propylbenzofuran-2-carboxylate (3.8 g) as a pink solid.

(e) Ethyl 6-hydroxy-7-propylbenzofuran-2-carboxylate

The ester product of step (d) was dissolved in ethyl acetate and reduced under hydrogen with palladium/-charcoal catalyst until uptake of hydrogen was complete. The solution was filtered and evaporated to leave ethyl 6-hydroxy-7-propylbenzofuran-2-carboxylate (2.8 g) as a pink solid.

(f) 6-[3-(4-Acetyl-3-hydroxy-2-propylphenoxy)-2-hydroxypropoxy]-7-propylbenzofuran-2-carboxylic acid The ester product of step (c) (2.8 g), 4-(2,3-epoxypropoxy)-2-hydroxy-3-propylacetophenone (3.0 g) and benzyl trimethylammonium hydroxide (0.1 g) in dimethylformamide were heated under reflux for 3 hours. The solvent was removed and the oil remaining dissolved in chloroform. The solution was washed with 5% sodium hydroxide solution and water, filtered and evaporated. The oil obtained was chromatographed on a silica column with chloroform/petroleum ether 40-60 as eluant. The appropriate fractions were combined and evaporated and the oil obtained hydrolysed by heating under reflux with aqueous/ethanolic sodium carbonate for 1 hour. Water was added and the solution acidified to give a brown solid.

The acid was purified by dissolving in benzene and precipitating with 40°–60° petroleum ether to give 6-[4-acetyl-3-hydroxy-2-propylphenoxy)-2-hydroxypropoxy]-7-propylbenzofuran-2-carboxylic acid (1.5 g) as a colourless solid mp 75°–80°.

Analysis: Found: C, 65.1; H, 6.5%. $C_{26}H_{30}O_8 \frac{1}{2}H_2O$ Requires: C, 65.1; H, 6.4%.

(g) Sodium 6-[3-(4-acetyl-3-hydroxy-2-propylphenoxy)-2-hydroxypropoxy]-7-propylbenzofuran-2-carboxylate The acid product of step (f) was dissolved in 25 ml of 0.1N sodium hydroxide solution by warming for 1 hour. The solution was filtered and freeze dried. Some water could not be removed in this manner and had to be removed as its benzene azeotrope. The solid obtained was triturated with acetone to give the sodium salt.

Analysis: Found: C, 60.0; H, 6.3%. $C_{26}H_{29}O_8 1\frac{1}{2}H_2O$ Requires: C, 60.0; H, 6.2%.

EXAMPLE 3

7-(3-[4-Acetyl-3-hydroxy-2-propylphenoxy]-2-hydroxypropoxy)-4-methyl-2-oxo-2H-1-benzopyran-3-acetic acid (a) Ethyl 7-hydroxy-4-methyl-2-oxo-2H-1-benzopyran-3-acetate To a prewashed suspension of sodium hydride (31.5 g of a 50% oil dispersion; 0.66 mole) in dry dimethylformamide (1.5 l) at room temperature was added dropwise over 30–40 minutes a solution of resacetophenone (45.6 g; 0.3 mole) in dry dimethylformamide (150 mls). The mixture was cooled to 5° and 3-methoxy-carbonylpropionyl chloride (105 g, 0.7 mole) was added dropwise over 45 minutes keeping the temperature below 10° C. The mixture was stirred at room temperature overnight, poured onto excess ice and dilute hydrochloric acid, and extracted with a 1:1 mixture of ether and ethyl acetate. The extract was washed thoroughly with 1% dilute hydrochloric acid, and water, and then with 5% sodium carbonate solution, and water. Drying and evaporation gave 2,4-bis(3-methoxycarbonylpropionyloxy)acetophenone (68 g) as a red oil, characterised by $^1$HNMR and MS. The oil (29 g) was set aside for 5 months, during which time spontaneous cyclisation to the 4-methylcoumarin occurred. The crystalline material was refluxed for 40 minutes with ethanol saturated with hydrogen chloride. The solution was diluted with water and extracted with ethyl acetate, which was washed with sodium bicarbonate solution and then evaporated to an oily solid. Chromatography over silica gel with dichloromethane containing ethyl acetate (5%), followed by crystallisation from ethyl acetate afforded ethyl 7-hydroxy-4-methyl-2-oxo-2H-1-benzopyran-3-acetate (3.6 g), mp 167°–168°.

Analysis: Found: C 63.6; H 5.3. $C_{14}H_{14}O_5$ Requires: C 64.1; H 5.4%.

(b) 7-(3-[4-Acetyl-3-hydroxy-2-propylphenoxy]-2-hydroxypropoxy)-4-methyl-2-oxo-2H-1-benzopyran-3-acetic acid A mixture of the product of step (a) (1.5 g, 0.006 mole) and 4-(2,3-epoxypropoxy)-2-hydroxy-3-propyl acetophenone (3.0 g, 0.012 mole) was refluxed in dry dimethylformamide (50 mls) containing 2 drops of benzyltrimethylammonium hydroxide for 2.5 hours. The mixture was poured into dilute hydrochloric acid (200 mls) and extracted into ethyl acetate, which was washed well with water, dried and evaporated to a red oil. This oil was hydrolysed with sodium carbonate (3 g) in refluxing ethanol for 30 minutes and the resulting sodium salt solution was washed well with ethyl acetate. Acidification of the aqueous layer gave an oily solid which was crystallised from ethyl acetate to give the title compound, mp 129.5°–130.5°.

Analysis: $C_{26}H_{28}O_9$ requires—Theory: C 64.45; H 5.8%. Found: C 64.51; H 5.64%.

(c) Sodium 7-(3-[4-acetyl-3-hydroxy-2-propylphenoxy]-2-hydroxypropoxy)-4-methyl-2-oxo-2H-1-benzopyran-3-acetate To a solution of the acid product of step (b) (0.481 g) in ethanol (15 mls) and water (5 mls) was added an equivalent amount of sodium bicarbonate (0.083 g) in water (25 ml). The mixture was warmed, filtered and freeze-dried to give the sub-title sodium salt (0.5 g).

Analysis: Found: C 59.3; H 5.2. $C_{26}H_{27}NaO_9H_2O$ Requires: C 59.5; H 5.5%.

EXAMPLE 4

Sodium 6-[5-(2-acetyl-3-hydroxyphenoxy)pentyloxy]naphthalene-2-carboxylate (a) 6-[5-(2-Acetyl-3-hydroxyphenoxy)pentyloxy]-naphthalene-2-carboxylic acid A suspension of 2-(5-bromopentyloxy)-6-hydroxy acetophenone (4.18 g), ethyl 6-hydroxynaphthalene-2-carboxylate (3 g) and potassium carbonate (1.92 g) in dry dimethylformamide (50 ml) was stirred for 60 hr, diluted with water and extracted with ethyl acetate. Evaporation and chromatography of the residue over silica with methylene chloride containing acetonitrile (1%) gave the ethyl ester of the sub-title compound as a crystalline solid (1.85 g). The ester (0.6 g) was refluxed in ethanol (100 ml) containing 40% sodium hydroxide solution (1 ml) for one hour. The solvent was removed and the residue was partitioned between water and ethyl acetate. Acidification of the aqueous layer gave the sub-title acid (0.50 g), mp 190°–193°.

(b) Sodium 6-[5-(2-acetyl-3-hydroxyphenoxy)pentyloxy]naphthalene-2-carboxylate

The acid of step (a) was converted to the sodium salt by the method of Example 1f.

EXAMPLE 5

Sodium 5-[3-(4-acetyl-3-hydroxy-2-propylphenoxy)propoxy]-4-(prop-2-enyl)benzofuran-2-carboxylate (a) Methyl 5-hydroxy-4-(prop-2-enyl)benzofuran-2-carboxylate A mixture of methyl 5-hydroxybenzofuran-2-carboxylate (4.14 g), potassium carbonate (5.95 g) and allyl bromide (3.73 ml) in dry acetone (100 ml) was refluxed and stirred for 16 hours. The solvent was evaporated and the residue was partitioned between water and ether. The ether was washed with water, dried and evaporated to give methyl 5-(prop-2-enyloxy)benzofuran-2-carboxylate (4.7 g) as a solid, characterised by NMR and mass spectral data. This ester (3.74 g) in N-methylpyrrolidinone (30 ml) was refluxed under nitrogen for 2 hr, cooled, and partitioned between water and ethyl acetate. The organic phase was washed with water, dried and evaporated to give the title ester (3.5 g), mp 114°–119°.

(b) Methyl 5-[3-(4-acetyl-3-hydroxy-2-propylphenoxy)propoxy]-4-(prop-2-enyl)benzofuran-2-carboxylate 4-(3-Bromopropoxy)-2-hydroxy-3-propylacetophenone (3.1 g), methyl 5-hydroxy-4-(prop-2-enyl)benzofuran-2-carboxylate (2.28 g), potassium carbonate (1.36 g) and dimethylformamide were stirred and heated at 90° for 3 hr. A further quantity of the bromopropoxy compound (3.1 g) and potassium carbonate (1.36 g) was added and the mixture was heated for a further 6 hr, cooled and partitioned between water and ethyl acetate. Evaporation of the organic phase followed by chromatography of the residue over silica with a mixture of petroleum ether (bp 60–80), dichloromethane, and ethyl acetate (10:10:1) furnished the title ester (2.5 g), mp 98°–99°.

(c) 5-[3-(4-Acetyl-3-hydroxy-2-propylphenoxy)propoxy]-4-(prop-2-enyl)benzofuran-2-carboxylic acid The ester of step (b) (1.43 g) was stirred in dioxan (30 ml) containing N sodium hydroxide (6.75 ml) for one hour. The green solution was acidified and extracted with ethyl acetate. Evaporation gave a residue which was chromatographed over silica with a mixture of dichloromethane, ether and formic acid (90:7:3) to give the title acid (0.7 g), mp 157°–158°.

(d) Sodium 5-[3-(4-acetyl-3-hydroxy-2-propylphenoxy)propoxy]-4-(prop-2-enyl)benzofuran-2-carboxylic acid The acid of step (c) was converted to the sodium salt by the method of Example 1f.

EXAMPLE 6

Sodium 6-{5-[2-acetyl-3-(prop-2-enyloxy)phenoxy]pentyloxy}naphthalene-2-carboxylate (a) 6-{5-[2-Acetyl-3-(prop-2-enyloxy)phenoxy]pentyloxy}naphthalene-2-carboxylic acid Ethyl 6-[5-(2-acetyl-3-hydroxyphenoxy)pentyloxy]naphthalene-2-carboxylate (1.85 g), potassium carbonate (0.59 g) and allyl bromide (0.74 ml) were stirred in dry dimethyl formamide (40 ml) for 20 hr. The mixture was diluted with water and extracted with ethyl acetate, which was washed with water, dried and evaporated to yield the ethyl ester of the sub-title compound (2.2 g) as a pale yellow solid. The ester (0.65 g) was hydrolysed by the method of Example 2f to give the title acid (0.36 g), mp 157°–157.5°.

(b) Sodium 6-{5-[2-acetyl-3-(prop-2-enyloxy)phenoxy]pentyloxy}naphthalene-2-carboxylate The acid of step (a) was converted to the sodium salt by the method of Example 1f.

EXAMPLE 7

Sodium 6-{5-[2-acetyl-3-hydroxy-4-(prop-2-enyl)phenoxy]pentyloxy}naphthalene-2-carboxylate (a) 6-{5-[2-Acetyl-3-hydroxy-4-(prop-2-enyl)phenoxy]pentyloxy}naphthalene-2-carboxylic acid Ethyl 6-{5-[2-acetyl-3-(prop-2-enyloxy)phenoxy]pentyloxy}naphthalene-2-carboxylate (1 g) was refluxed in N-methylpyrrolidinone (10 ml) under nitrogen for 3.5 hr. The mixture was partitioned between water and ethyl acetate. The organic phase was washed with water and evaporated, and the residue was chromatographed over silica with a mixture of light petroleum (bp 60–80) and ethyl acetate (5:1) to give the ethyl ester of the sub-title compound (0.61 g). The ethyl ester (0.58 g) was hydrolysed by the method of Example 2f to give the title acid (0.46 g), mp 172°–172.5°.

(b) Sodium 6-{5-[2-acetyl-3-hydroxy-4-(prop-2-enyl)phenoxy]pentyloxy}naphthalene-2-carboxylate The acid of step (a) was converted to the sodium salt by the method of Example (1f).

EXAMPLE 8

Sodium 3-methyl-6-(5-phenylpentylthio)-7-propylbenzo[b]furan-2-carboxylate (a) 2-Hydroxy-4-(5-phenylpentylthio)-3-propylacetophenone A mixture of 5-bromopentylbenzene (1.93 g), 2-hydroxy-4-mercapto-3-propylacetophenone (1.78 g), potassium carbonate (1.28 g), and potassium iodide (0.1 g) in dry dimethylformamide (60 ml) under nitrogen was heated at 60° for 20 hr. The mixture was partitioned between ethyl acetate and dilute hydrochloric acid. The organic phase was washed with water, dried and evaporated to an oil which was chromatographed on silica with a mixture of petroleum ether (bp 40°–60°) and ether (9:1) to give the sub-title compound (1.85 g), mp 82°–83°.

(b) 3-Methyl-6-(5-phenylpentylthio)-7-propybenzo[b]furan-2-carboxylic acid

To the product of step (a) (1.0 g) and sodium hydride (0.135 g) in dry dimethylformamide (20 ml) was added ethyl chloroacetate (0.35 g) in dimethylformamide (3 ml). The mixture was stirred for 2 hr at 80°, poured into dilute hydrochloric acid and extracted with ethyl acetate. Evaporation of the solvent and chromatography of the residue over silica with a mixture of petroleum ether (bp 40°–60°) and ether (85:15) gave the ethyl ester of the sub-title compound (0.063 g), which was refluxed for 3 hr in ethanol containing N sodium hydroxide (0.5 ml). Evaporation and acidification afforded a solid, which was chromatographed on silica (dichloromethane-methanol, 93:7) to yield the sub-title compound (0.012 g), mp 128°–130°.

(c) Sodium 3-methyl-6-(5-phenylpentylthio)-7-propylbenzo[b]furan-2-carboxylate

The product from step (b) was converted to the title compound by the method of Example 1f.

EXAMPLE 9

Sodium [5-{5-(4-methoxy-3-propylphenyl)pentyloxy}-1-naphthalenyloxy]acetate (a) Ethyl [5-{5-(4-methoxy-3-propylphenyl)pentyloxy}-1-naphthalenyloxy]acetate To a stirred suspension of 5-(4-methoxy-3-propylphenyl)pentanol (2.48 g), ethyl (5-hydroxy-1-naphthalenyloxy)acetate (2 g), and triphenylphosphine (3.2 g) in dry tetrahydrofuran (30 ml) under nitrogen was added diethyl azodicarboxylate (1.65 ml) slowly so that the temperature did not rise above 50°. After 3 hours the solution was evaporated, and the residue was chromatographed on silica with a mixture of dichloromethane and light petroleum (bp 40°–60°) (4:6) to give the sub-title ester (3 g), mp 70° (from ethanol).

(b) Sodium [5-{5-(4-methoxy-3-propylphenyl)pentyloxy}-1-naphthalenyloxy]acetate

The ester of step (a) was hydrolysed by the method of Example 2(f) to give the acid of the title salt, mp 169°–170°. This acid was converted to the title sodium salt by the method of Example 1(f).

EXAMPLE 10

Acids and sodium salts prepared by the process of Example 5

A. 5-[3-(4-Acetyl-3-hydroxy-2-propylphenoxy)propoxy]benzofuran-2-carboxylic acid, mp 154°–157°.
B. 6-[3-(4-Acetyl-3-hydroxy-2-propylphenoxy)propoxy]-7-methylbenzofuran-2-carboxylic acid, mp 197°–199°.
C. 6-[3-(4-Acetyl-3-amino-2-propylphenylthio)propoxy]-7-methylbenzofuran-2-carboxylic acid, mp 166°–168°.
D. 6-[3-(4-Chloro-3-methylphenoxy)propoxy]-7-methylbenzofuran-2-carboxylic acid, mp 195°–197°.
E. 5-[3-(4-Acetyl-3-hydroxy-2-propylphenoxy)propoxy]-2-methylindole-3-carboxylic acid, mp 180°–181° (decomp.).
F. 5-[3-(4-Acetyl-3-hydroxy-2-propylphenoxy)-propyloxy]benzothiophene-2-carboxylic acid.
G. 6-[3-(4-Acetyl-3-hydroxy-2-propylphenoxy)-propyloxy]-7-methyl-5(prop-2-enyl)benzofuran-2-carboxylic acid.

Acids and sodium salts prepared by the process of Example 1

H. 7-(3-[4-Acetyl-3-hydroxy-2-propylphenoxy]-2-hydroxy propoxy)naphthalene-2-carboxylic acid, mp 179°–181°.

Acids and sodium salts prepared by the process of Example 4

I. 6-(3-[4-Acetyl-3-hydroxy-2-propylphenoxy]propoxy)naphthalene-2-carboxylic acid, mp 188°–189°.
J. ({7-(3-[4-Acetyl-3-hydroxy-2-propylphenoxy]-propoxy)-2-naphthalenyl}oxy)acetic acid, mp 159°–161°.
K. 7-(3-[4-Acetyl-3-hydroxy-2-propylphenylthio)-propoxy]naphthalene-2-carboxylic acid, mp 181°–182°.
L. 7-[3-(4-chloro-3-methylphenoxy)propoxy]naphthalene-2-carboxylic acid, mp 163°–165°.
M. 7-[2-(4-Acetyl-3-hydroxy-2-propylphenoxy)ethoxy]naphthalene-2-carboxylic acid, mp 184°–185°.
N. [{7-(3-[4-Acetyl-3-hydroxy-2,6-dipropylphenoxy]propoxy)-2-naphthalenyl}oxy]acetic acid, mp 133°–134°.
O. 6-[3-(4-Acetyl-3-hydroxy-2-propylphenoxy)propoxy]-α-methylnaphthalene-2-acetic acid, mp 145°–147°.
P. 6-[3-(4-Acetyl-3-hydroxy-2-propylphenoxy)propoxy]naphthalene-2-acetic acid, mp 122° (dec)
Q. [{5-(3-[3-Formyl-2-(2-propenyl)phenoxy]propoxy)-1-naphthalenyl}oxy]acetic acid, mp 161°–162°.
R. [{5-(5-[4-Methoxy-3-propylphenyl]pentyloxy)-1-naphthalenyl}oxy]acetic acid,
S. 7-{3-(4-Acetyl-3-hydroxy-2-propylphenoxy)-propyloxy}-2-naphthalenepropanoic acid.

EXAMPLE 11

Sodium 6-{3-[4-acetyl-3-(2-propenyloxy)-2-propylphenoxy]-propoxy}-7-methylbenzofuran-2-carboxylate (a) Methyl 6-[3-(4-acetyl-3-(2-propenyloxy)-2-propylphenoxy)propoxy]-7-methylbenzofuran-2-carboxylate 2,6-Dihydroxytoluene was converted by the methods of Example 2(a), (b) and (c) to methyl 2-[3-benzyloxy-6-formyl-2-methylphenoxy]acetate, mp 64°–66°, which by the methods of Example 2(d) and (e) and Example 5(b) gave successively methyl 6-benzyloxy-7-methylbenzofuran-2-carboxylate, mp 117°–120° (from ethyl acetate), methyl 6-hydroxy-7-methylbenzofuran-2-carboxylate, mp 144°–147° (decomp.) and methyl 6-[3-(4-acetyl-3-hydroxy-2-propylphenoxy)propoxy]-7-methylbenzofuran-2-carboxylate, mp 123°–124° from methanol).

This last ester (1.1 g), potassium carbonate (0.41 g), allyl bromide (0.75 g) and potassium iodide (2 crystals) in dry dimethylformamide (20 ml) were heated at 100° for two days under nitrogen. The cooled reaction mixture was poured into water and extracted with ethyl acetate. The combined extracts were washed with aqueous sodium carbonate solution, water and dried. Solvent was removed to give an oil which was chromatographed on silica gel to give the sub-title compound (0.41 g), recrystallised from cyclohexane, mp 80°–83°.

(b) Sodium 6-{3-[4-acetyl-3-(2-propenyloxy)-2-propylphenoxy]propoxy}-7-methylbenzofuran-2-carboxylate The ester from step (a) was hydrolysed by the method of Example 5(c) to give the acid of the title sodium salt, mp 159°–161° (from ethanol). This acid was converted to the title sodium salt by the method of Example 1(f).

EXAMPLE 12

Preparation of Intermediates (a) 5-(4-Methoxy-3-propylphenyl)pentanol

Aluminium chloride (112 g) was slowly added over one hour to a stirred mixture of o-propylanisole (60 g), glutaric anhydride (50.5 g), tetrachloroethane (880 ml) and nitrobenzene (200 ml) maintained between 3°–4°. The mixture was stirred for two days and then poured into dilute hydrochloric acid. The organic phase was steam distilled, and the residue remaining was extracted with ether, which was then extracted with sodium bicarbonate solution. Acidification and crystallisation from ethylacetate-light petroleum (bp 60°–80°) gave 5-oxo-5-(4-methoxy-3-propylphenyl)pentanoic acid (70 g), mp 105°–106°. This acid was refluxed with zinc amalgam (270 g), dioxan (300 ml), toluene (300 ml), and concentrated hydrochloric acid (100 ml) for two days. Extraction with ether and subsequent evaporation gave an oil, which crystallised from cyclohexane to give 5-(4-methoxy-3-propylphenyl)pentanoic acid (36 g), mp 84°. This acid was esterified with methanol and concentrated sulphuric acid, and the methyl ester so obtained (26 g) was added to a stirred suspension of lithium aluminium hydride (3 g) in tetrahydrofuran at 0°. The mixture was refluxed for 3 hours, cooled, treated with water, and extracted with ether, which on evaporation gave the title alcohol (16 g), mp 34.5°–35°.

(b) 5-(3-Bromopropoxy)-2-chlorotoluene

4-Chloro-m-cresol (4.25 g), 1,3-dibromopropane (60 g), N sodium hydroxide solution (30 ml), and benzyl triethylammonium chloride (6.95 g) were stirred vigorously for 18 hours. The mixture was extracted with dichloromethane, which was washed with water and evaporated. The residue was distilled at 170°–180°/0.05 mm Hg to give the title ether (5.3 g) as an oil.

Similarly were prepared 3-(3-bromopropyloxy)-2-(2-propenyl)benzaldehyde, bp 170°/0.05 mm Hg, and
4-(3-bromopropyloxy)-2-hydroxy-3,5-dipropylacetophenone, bp 220°-225°/0.05 mm Hg.

(c) 2-Amino-4-(3-bromopropylthio)-3-propylacetophenone

2-Amino-4-mercapto-3-propylacetophenone (4.2 g, prepared by well-known procedures) in dimethyl formamide (20 ml) was slowly added to a stirred mixture of 1,3-dibromopropane (32 g) and potassium carbonate (3.02 g) in dimethylformamide (150 ml) at 50° under nitrogen. After one hour the mixture was diluted with water and extracted with ethyl acetate, which was evaporated to yield a red oil. Distillation at 250°/0.05 mm Hg gave the title ether (4.9 g), characterised by $^1$H NMR and MS.

(d) Ethyl [(5-hydroxy-1-naphthalenyl)oxy]acetate

Ethyl chloroacetate (24.5 g) was added slowly with stirring to a clear solution prepared from 1,5-naphthalenediol (32 g) and sodium hydride (4.8 g) in dimethylformamide (200 ml) and the mixture was warmed to 60° for 2 days. The solvent was evaporated and the residue was extracted with ethyl acetate, which was washed with water, dried, and evaporated to yield a solid (46 g). Chromatography over silica with a mixture of light petroleum (bp 60°-80°) and ether (3:1) gave the title ester, mp 186°-188°.

We claim:

1. A compound of formula I,

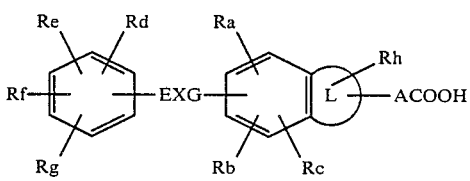

in which
Ra, Rb, Rc, Rd, Re, Rf and Rg, which may be the same or different, each represent hydrogen, amino, hydroxy, alkoxy, alkenyloxy, halogen, acyl, alkenyl, alkyl, or alkoxy substituted by phenyl,
Rh is hydrogen, alkyl or —COOH,
X is a hydrocarbon chain containing from 2 to 10 carbon atoms and optionally substituted by a hydroxy group,
A has no significance or represents Y, OY, or SY and Y represents a C 1 to 4 hydrocarbon chain which is optionally substituted by alkyl C 1 to 4,
E and G, which may be the same or different, each represent —O—, —S— or —CH$_2$—, provided that at least one of E and G is —O— or —S—,
L, together with the carbon atoms to which it is attached, forms a benzene or pyran-2-one ring,
Ra, Rb, Rc, Rd, Re, Rf, Rg and Rh, when they contain carbon, each containing less than 7 carbon atoms,
and pharmaceutically acceptable salts, esters and amides thereof.

2. A compound according to claim 1, wherein Ra to Rg are selected from hydrogen, acetyl, formyl, hydroxy, methyl, propyl, allyl, allyloxy and chlorine.

3. A compound according to claim 1, wherein none, or only one, of Ra, Rb and Rc are other than hydrogen and two, three or four of Rd, Re, Rf and Rg are other than hydrogen.

4. A compound according to claim 3, wherein an adjacent three of Rd, Re, Rf and Rg are acetyl, hydroxy and propyl.

5. A compound according to claim 1, where A is not present or is Y or OY and Y is —CH$_2$— or —CH(CH$_3$)—.

6. A compound according to claim 1, wherein E and G are both oxygen or one is oxygen and the other is sulphur.

7. A compound according to claim 1, wherein E and G are both oxygen, Ra, Rb and Rc each represent hydrogen, alkyl or alkenyl, Rd, Re, Rf and Rg, each represent hydrogen, hydroxy, alkoxy, acyl, alkenyl, alkyl or alkoxy substituted by phenyl, Rh is hydrogen, A has no significance and L is a benzene ring.

8. A compound according to claim 1, wherein E and G are both oxygen, Rg, Ra and Rb are all hydrogen, Rc, Rd, Re and Rf are hydrogen, hydroxy, alkanoyl, alkenyl or alkyl and the ring L, together with the group —A—COOH is of formula,

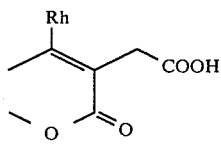

in which Rh is hydrogen or alkyl.

9. A compound according to claim 1 and selected from 7-(3-[4-Acetyl-3-hydroxy-2-propylphenoxy]-2-hydroxypropoxy)-8-propylnaphthalene-2-carboxylic acid, 7-(3-[4-Acetyl-3-hydroxy-2-propylphenoxy]-2-hydroxypropoxy)-4-methyl-2-oxo-2H-1-benzopyran-3-acetic acid, 6-[5-(2-Acetyl-3-hydroxyphenoxy)pentyloxy]naphthalene-2-carboxylic acid, 6-{5-[2-Acetyl-3-(prop-2-enyloxy)phenoxy]pentyloxy}naphthalene-2-carboxylic acid, 6-{5-[2-Acetyl-3-hydroxy-4-(prop-2-enyl)phenoxy]pentyloxy}naphthalene-2-carboxylic acid,

[5-{5-(4-Methoxy-3-propylphenyl)pentyloxy)}-1-naphthalenyloxy]acetic acid, 7-(3-[4-Acetyl-3-hydroxy-2-propylphenoxy]-2-hydroxypropoxy)naphthalene-2-carboxylic acid, 6-(3-[4-Acetyl-3-hydroxy-2-propylphenoxy]propoxy)naphthalene-2-carboxylic acid, ({7-(3-[4-Acetyl-3-hydroxy-2-propylphenoxy]propoxy)-2-naphthalenyl}oxy)acetic acid, 7-(3-[4-Acetyl-3-hydroxy-2-propylphenylthio)propoxy]naphthalene-2-carboxylic acid, 7-(3-[4-Chloro-3-methylphenoxy)propoxy]naphthalene-2-carboxylic acid, 7-[2-(4-Acetyl-3-hydroxy-2-propylphenoxy)ethoxy]naphthalene-2-carboxylic acid,

[{7-(3-[4-Acetyl-3-hydroxy-2,6-dipropylphenoxy]propoxy)-2-naphthalenyl}oxy]acetic acid, 6-[3-(4-Acetyl-3-hydroxy-2-propylphenoxy)propoxy]-α-methylnaphthalene-2-acetic acid, 6-[3-(4-Acetyl-3-hydroxy-2-propylphenoxy)propoxy]-naphthalene-2-acetic acid,

[{5-(3-[3-Formyl-2-(2-propenyl)phenoxy]propoxy)-1-naphthalenyl}oxy]acetic acid,

[{5-(5-[4-Methoxy-3-propylphenyl]pentyloxy)-1-naphthalenyl}oxy]acetic acid,

7-{3-(4-Acetyl-3-hydroxy-2-propylphenoxy)propyloxy)}-2-naphthalenepropanoic acid, and the sodium salts of any one thereof.

10. A pharmaceutical formulation comprising an effective anti SRS-A amount of a compound according to claim 1 in admixture with a pharmaceutically acceptable adjuvant, diluent or carrier.

11. A method of treatment of a disorder in which SRS-A is a factor, which comprises administration of an effective amount of a compound according to claim 1 to a patient suffering from such a condition.

* * * * *